United States Patent
Kanamori et al.

(10) Patent No.: US 6,806,367 B2
(45) Date of Patent: Oct. 19, 2004

(54) PROCESS FOR PRODUCING CARBONYL HYDRAZONES

(75) Inventors: Fumio Kanamori, Shiga (JP); Masamitsu Tsukamoto, Mayfield Heights, OH (US)

(73) Assignee: Ishihara Sangyo Kaisha, Ltd., Osaka (JP)

( * ) Notice: Subject to any disclaimer, the term of this patent is extended or adjusted under 35 U.S.C. 154(b) by 86 days.

(21) Appl. No.: 09/983,835

(22) Filed: Oct. 26, 2001

(65) Prior Publication Data

US 2003/0187264 A1 Oct. 2, 2003

(51) Int. Cl.[7] .................. C07D 43/02; C07D 239/54; C07C 251/16
(52) U.S. Cl. ............... 544/310; 544/311; 544/60; 544/123; 544/295; 564/229; 564/247; 564/147
(58) Field of Search .................... 544/60, 123, 295, 544/310, 311; 564/229, 247, 147

(56) References Cited

U.S. PATENT DOCUMENTS

| | | | |
|---|---|---|---|
| 4,270,947 A | * 6/1981 | Gutman | 504/303 |
| 4,855,309 A | * 8/1989 | Koch et al. | 514/346 |
| 5,521,290 A | * 5/1996 | Sivam et al. | 530/391.5 |
| 5,672,466 A | * 9/1997 | Okamura et al. | 430/336 |
| 6,333,296 B1 | 12/2001 | Pulman et al. | 504/243 |
| 6,479,435 B1 | 11/2002 | Pulman et al. | 504/242 |
| 2002/0161224 A1 | * 10/2002 | Pulman et al. | 544/236 |
| 2003/0096990 A1 | * 5/2003 | Read et al. | 544/60 |

FOREIGN PATENT DOCUMENTS

EP 149242 * 7/1985

OTHER PUBLICATIONS

March J., "Advanced Organic Chemistry—Reactions, Mechanisms, and Structure", 4th Edition, (c) 1992, pp. 1141–1142.*

* cited by examiner

Primary Examiner—Richard L. Raymoni
Assistant Examiner—Tamthom N. Truong
(74) Attorney, Agent, or Firm—Sughrue Mion, PLLC

(57) ABSTRACT

This invention relates to a method for producing compounds of the formula (I) or their salts:

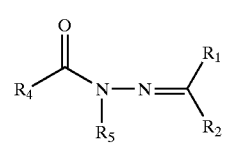

(I)

wherein each of $R_1$ and $R_2$ is hydrogen, unsubstituted or substituted alkyl, unsubstituted or substituted alkenyl, unsubstituted or substituted alkynyl, unsubstituted or substituted aryl, unsubstituted or substituted heteroaryl, $OR_3$, $SR_3$, $COR_3$, $COOR_3$ or cyano;

$R_1$ and $R_2$ may combine together with the adjacent carbon atom of $=CR_1R_2$ to form an unsubstituted or substituted cyclic ring;

each of $R_4$ and $R_5$ is hydrogen, unsubstituted or substituted alkyl, unsubstituted or substituted alkenyl, unsubstituted or substituted alkynyl, unsubstituted or substituted aryl, unsubstituted or substituted heteroaryl, $NR_6R_7$, $OR_8$ or $SR_9$;

$R_4$ and $R_5$ may combine together with the adjacent skeleton of C/N bond to form a heterocyclic ring;

which comprises rearranging compounds of the formula (II) or their salts:

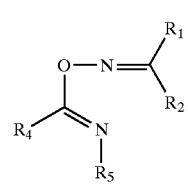

(II)

wherein $R_1$, $R_2$, $R_4$ and $R_5$ are as defined above.

4 Claims, No Drawings

PROCESS FOR PRODUCING CARBONYL HYDRAZONES

The present invention relates to a process for producing carbonyl hydrazones, their intermediates and the like.

BACKGROUND OF THE INVENTION

Certain herbicidal compounds such as 1-amino-3-substituted-phenyl-2,4(1H,3H)-pyrimidinediones and processes for their preparations are disclosed in WO98/41093, and the like.

It has been required that these compounds can be produced by using appropriate processes for industrial exploitations in terms of yields, raw materials, reaction steps, reaction operations, economical stand points etc.

The present inventors have conducted researches and investigations for these processes. As a result, they have obtained facts and discoveries that these compounds can be prepared using certain rearrangement reactions of substituted aminooxy compounds and that such rearrangement reactions are novel.

SUMMARY OF THE INVENTION

The first aspect of the present invention is to provide a method for producing carbonyl hydrazones of the formula (I) or their salts:

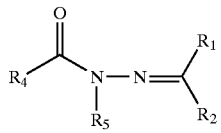

wherein each of $R_1$ and $R_2$ is hydrogen, unsubstituted or substituted alkyl, unsubstituted or substituted alkenyl, unsubstituted or substituted alkynyl, unsubstituted or substituted aryl, unsubstituted or substituted heteroaryl, $OR_3$, $SR_3$, $COR_3$, $COOR_3$ or cyano; $R_3$ is unsubstituted or substituted alkyl, unsubstituted or substituted alkenyl, unsubstituted or substituted alkynyl, unsubstituted or substituted aryl, or unsubstituted or substituted heteroaryl;

$R_1$ and $R_2$ may combine together with the adjacent carbon atom of $=CR_1R_2$ to form an unsubstituted or substituted cyclic ring;

each of $R_4$ and $R_5$ is hydrogen, unsubstituted or substituted alkyl, unsubstituted or substituted alkenyl, unsubstituted or substituted alkynyl, unsubstituted or substituted aryl, unsubstituted or substituted heteroaryl, $NR_6R_7$, $OR_8$ or $SR_9$; each of $R_6$, $R_7$, $R_8$ and $R_9$ is hydrogen, unsubstituted or substituted alkyl, unsubstituted or substituted alkenyl, unsubstituted or substituted alkynyl, unsubstituted or substituted aryl, unsubstituted or substituted heteroaryl, unsubstituted or substituted alkylcarbonyl, unsubstituted or substituted alkenylcarbonyl, unsubstituted or substituted alkenylcarbonyl, unsubstituted or substituted arylcarbonyl, or unsubstituted or substituted heteroarylcarbonyl;

$R_4$ and $R_5$ may combine together with the adjacent skeleton of C/N bond to form a heterocyclic ring;

which comprises rearranging substituted aminooxy compounds of the formula (II) or their salts:

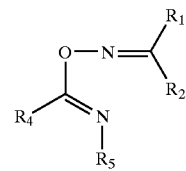

wherein $R_1$, $R_2$, $R_4$ and $R_5$ are as defined above.

The second aspect of the present invention is to provide a process for producing 1-substituted amino-2,4(1H,3H)-pyrimidinediones of the formula (I-a) or their salts:

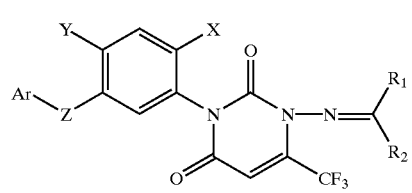

wherein $R_1$ and $R_2$ are as defined above;
each of X and Y is hydrogen, halogen, cyano, nitro, thiocarbamoyl or haloalkyl;
Z is oxygen, sulfur or NR; R is hydrogen, alkyl, alkenyl or alkynyl;
Ar is unsubstituted or substituted aryl, or unsubstituted or substituted heteroaryl;
which comprises rearranging 2-(substituted aminooxy)-4-(3H) pyrimidinones of the formula (II-a) or their salts:

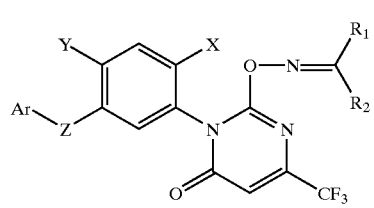

wherein $R_1$, $R_2$, X, Y, Z and Ar are as defined above.

Among the compounds of the formula (I), said 1-substituted amino-2,4(1H,3H)-pyrimidinediones of the formula (I-a) or their salts are useful in view of the preparation processes of herbicidal and/or desiccant compounds.

The third aspect of the present invention is to provide 2-(substituted-aminooxy)-4-(3H) pyrimidinones of the formula (II-a) or their salts, and to provide a process for producing 2-(substituted aminooxy)-4-(3H) pyrimidinones of the formula (II-a) or their salts:
which comprises reacting 2-halogeno-4-(3H) pyrimidinones of the formula (III-a) or their salts:

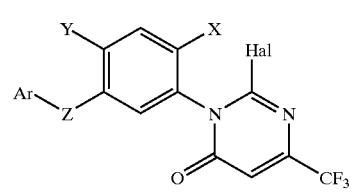

wherein Hal is halogen, X, Y, Z and Ar are as defined above, with oxime derivatives of the formula (IV) or their salts:

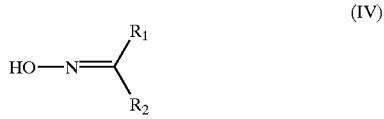

wherein $R_1$ and $R_2$ are as defined above.

The fourth aspect of the present invention is to provide 2-halogeno-4-(3H) pyrimidinones of the formula (III-a) or their salts, and to provide a process for producing 2-halogeno-4-(3H) pyrimidinones of the formula (III-a) or their salts:

which comprises reacting 2,4(1H,3H)-pyrimidinediones of the formula (V-a) or their salts:

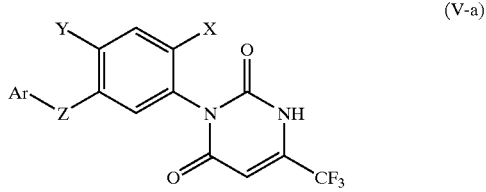

wherein X, Y, Z and Ar are as defined above, with a halogenating agent.

DETAILED DESCRIPTION OF THE INVENTION

In the above definitions, for formulas (I), (II), (I-a), (II-a), (III-a), (IV) and (V-a), the substituent for the substituted alkyl the substituted alkenyl, the substituted alkynyl, the substituted alkylcarbonyl, the substituted alkenylcarbonyl or the substituted alkynylcarbonyl may, for example, be halogen, alkoxy, haloalkoxy, alkylthio, alkylsulfinyl, alkylsulfonyl, dialkylaminocarbonyl, cyano, nitro, alkylsulfonylamino, alkoxycarbonylalkoxy, alkylcarbonylamino, amino, alkylamino, dialkylamino, alkoxycarbonyl, alkylcarbonyl, alkenylcarbonyl, alkynylcarbonyl, arylcarbonyl, heteroarylcarbonyl, alkylcarbonyloxy, alkenylcarbonyloxy, alkynylcarbonyloxy, arylcarbonyloxy, heteroarylcarbonyloxy and the like. The number of substituents may be one or more. When the substituents are two or more, they may be the same or different from each other.

In the definitions for formulas (I), (II), (I-a), (II-a), (III-a), (IV) and (V-a),the substituent for the substituted aryl, the substituted heteroaryl, the substituted arylcarbonyl or the substituted heteroarylcarbonyl may, for example, be halogen, alkyl, alkenyl, alkynyl, haloalkyl, haloalkenyl, haloalkynyl, alkoxy, haloalkoxy, alkenyloxy, haloalkenyloxy, alkynyloxy, haloalkynyloxy, alkylthio, alkylsulfinyl, alkylsulfonyl, dialkylaminocarbonyl, cyano, nitro, alkylsulfonylamino, alkoxycarbonylalkoxy, alkylcarbonylamino, bisbenzoylamino, amino, alkylamino, dialkylamino, alkoxycarbonyl, alkylcarbonyl, alkenylcarbonyl, alkynylcarbonyl, arylcarbonyl, heteroarylcarbonyl, alkylcarbonyloxy, alkenylcarbonyloxy, alkynylcarbonyloxy, arylcarbonyloxy, heteroarylcarbonyloxy, aryl, heteroaryl and the like. The number of substituents may be one or more. When the substituents are two or more, they may be the same or different from each other.

Further, in the definitions for formulas (I), (II), (I-a), (II-a), (III-a), (IV) and (V-a), the substituent for the substituted cyclic ring, for $R_1$ and $R_2$, or the substituent for the substituted heterocyclic ring, for $R_4$ and $R_5$, may, for example, be halogen, alkyl, alkenyl, alkynyl, haloalkyl, haloalkenyl, haloalkynyl, alkoxy, haloalkoxy, alkenyloxy, haloalkenyloxy, alkynyloxy, haloalkynyloxy, alkylthio, alkylsulfinyl, alkylsulfonyl, dialkylaminocarbonyl, cyano, nitro, alkylsulfonylamino, alkoxycarbonyalkoxy, alkylcarbonylamino, amino, alkylamino, dialkylamino, alkoxycarbonyl, alkylcarbonyl, alkenylcarbonyl, alkynylcarbonyl, arylcarbonyl, heteroarylcarbonyl, alkylcarbonyloxy, alkenylcarbonyloxy, alkynylcarbonyloxy, arylcarbonyloxy, heteroarylcarbonyloxy and the like. The number of substituents may be one or more. When the substituents are two or more, they may be the same or different from each other.

The alkyl and alkyl moiety in said definitions may be a straight or branched chain having 1 to 6 carbon atoms, preferably 1 to 4 carbon atoms. The alkyl group may include methyl, ethyl, propyl, butyl, pentyl or hexyl. The alkenyl and alkenyl moiety therein may be a straight or branched chain having 2 to 6 carbon atoms, preferably 2 to 4 carbon atoms. The alkenyl group may include vinyl, propenyl, butenyl, pentenyl or hexenyl. The alkynyl and alkynyl moiety therein may be a straight or branched chain having 2 to 6 carbon atoms, preferably 2 to 4 carbon atoms. The alkynyl group may include ethynyl, propynyl, butynyl, pentynyl or hexynyl.

The aryl or heteroaryl, or its moiety therein may be a carbon containing aromatic ring having at least five membered with or without saturated or unsaturated bonds. The aryl group may include phenyl, naphthyl or indenyl. The heteroaryl group may include pyridyl, pyrimidinyl, pyridazinyl, triazolyl, thiazolyl, thienyl, furyl, isothiazolyl, quinolyl or quinoxalinyl.

The cyclic ring for $R_1$ and $R_2$ may be 3 to 8 membered ring, and may be a saturated or unsaturated cyclic ring containing from 0 to 4 heteroatoms selected from oxygen, sulfur and nitrogen. The cyclic ring may, for example, be cyclopentylidene, cyclohexylidene, cyclopent-3-enylidene, tetrahydropyran-4-ylidene, tetrahydrothiopyran-4-ylidene, 1-methylpiperidin-4-ylidene, 1,3-dithiolan-2-ylidene, [1,3,5]dioxathian-2-ylidene or 2,2,-dimethyl-4,6-dioxo-[1,3]dioxan-5-ylidene.

The heterocyclic ring for $R_4$ and $R_5$ may be 3–8 membered ring, and may contain from 0 to 4 heteroatoms selected from oxygen, sulfur and nitrogen, other than the nitrogen atom adjacent to R5 group in the formulas (I) and (II). The heterocyclic ring for (I) may, for example, be 2-oxo-2H-pyridin-1-yl, 6-oxo-6H-pyridazin-1-yl, 3-oxo-3H-[1,2,4]triazin-2-yl, 2-oxo-2H-[1,3,5]triazin-1-yl, 2-oxo-3-phenyl-2, 3-dihydroimidazol-1yl, 2, -dioxo-3-phenyl-3, 4-dihydro-2H-pyrimidin-1-yl, 2-oxo-3-phenyltetrahydropyrimidin-1-yl, 4-oxo-5-phenyl-[1,3,5]thiadiazinan-3-yl, 4-oxo-5-phenyl-[1,3,5]oxadiazinan-3-yl or 1-oxo-1H-isoquinolin-2-yl.

The halogen atom and halogeno part in said definitions is fluorine, chlorine, bromine or iodine. The number of halogen atom of said halogeno part is one or more. When the number of halogen atom is two or more, halogen atoms may be the same or different each other.

Some compounds of the formulas (I), (II), (I-a), (II-a), (III-a), (IV) and (V-a) may form salts with acidic substances or basic substances. The salts with acidic substances may be inorganic acid salts such as hydrochloride, hydrobromide, phosphate, sulfate or nitrate. The salts with basic substances may be salts of inorganic or organic bases such as sodium salt, potassium salt, calcium salt, quarternary ammonium salt such as ammonium salt or dimethylamine salt.

Further some compounds of the formulas (I), (II), (I-a), (II-a), (III-a), (IV) and (V-a) may include isomers.

In the above method for producing compounds of the formula (I) or their salts, rearrangement reactions are usually conducted by heating compounds of the formula (II) or their salts in the presence or absence of a solvent.

The solvent may include aromatic hydrocarbons such as benzene, toluene, xylene, mesitylene, chlorobenzene or anisole; aliphatic hydrocarbons such as cyclohexane or octane; ethers such as tert-butyl ethyl ether, di-isobutyl ether or 1,4-dioxane; nitrites such as butyronitrile or isobutyronitrile; etc. They may be used alone as a single compound or in combination. The amount of a solvent is usually from 0 to 10 parts by volume, preferably from 0 to 5 parts by volume, per one part by weight of the compounds of the formula (II).

The reaction temperature is usually from 50 to 200° C., preferably from 100 to 180° C. The reaction time is usually from 5 minutes to 24 hours, preferably from 30 minutes to 8 hours.

The reaction can be carried out under drying atmosphere, preferably an inert atmosphere such as nitrogen gas or argon gas.

After completion of the reaction, the product is isolated by ordinary post-treatment e.g. addition of water and extraction with an organic solvent. If necessary, the product may be purified by refinery methods such as distillation, crystallization or chromatography.

The method of rearrangement reactions of the present invention can be also applied to a process for producing 1-substituted amino-2,4(1H,3H)-pyrimidinediones of the formula (I-a) or their salts by using 2-(substituted aminooxy)-4-(3H)-pyrimidiones of the formula (II-a) or their salts.

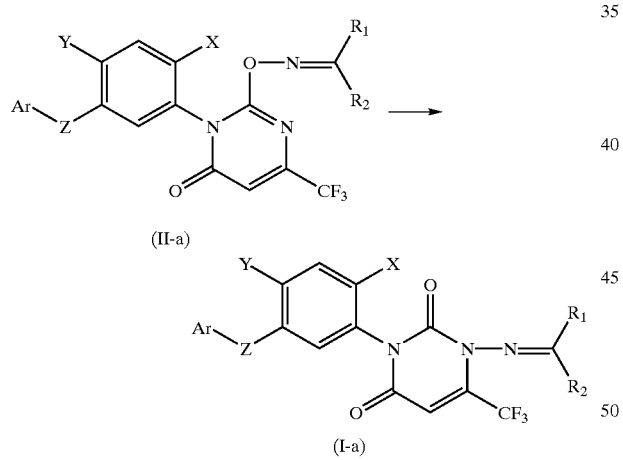

(II-a)

(I-a)

The rearrangement reactions are conducted at the same or similar conditions as the above method.

Among the 2-(substituted aminooxy)-4-(3H) pyrimidinones of the formula (II-a), the following compounds or their salts may be used preferably as the starting materials of the above process:

(1) The compounds, wherein X is hydrogen or halogen, Y is halogen, cyano, nitro or haloalkyl, Z is oxygen, sulfur or NR, R is alkyl, and Ar is phenyl, pyridyl, pyrimidinyl or quinolyl and each of the phenyl, pyridyl, pyrimidinyl or quinolyl may be substituted with at least one substituent selected from the group consisting of halogen, alkyl, haloalkyl, alkoxy, haloalkoxy, alkylthio, alkylsulfinyl, alkylsulfonyl, dialkylaminocarbonyl, cyano, nitro, alkylsulfonylamino, alkoxycarbonylalkoxy, alkylcarbonylamino, bisbenzoylamino, amino, alkylamino, dialkylamino, alkoxycarbonyl, alkylcarbonyl, alkenylcarbonyl, alkynylcarbonyl, arylcarbonyl, heteroarylcarbonyl, alkylcarbonyloxy, alkenylcarbonyloxy, alkynylcarbonyloxy, arylcarbonyloxy and heteroarylcarbonyloxy, $R_1$ and $R_2$ are as defined above.

(2) The compounds, wherein X is hydrogen or fluorine, Y is chlorine, cyano, nitro or trifluoromethyl, Z is oxygen, sulfur or methylimino and Ar is phenyl, 2-iodophenyl, 2-trifluoromethoxyphenyl, 2-nitrophenyl, 4-nitrophenyl, 4-methylsulfonylaminophenyl, 4-(1-ethoxycarbonylethoxy)phenyl, 2-cyanophenyl, 3-cyanophenyl, 2-cyano-3-fluorophenyl, 2-cyano-4-fluorophenyl, 2-cyano-4-nitrophenyl, 4-nitro-2-trifluoromethylphenyl, 4-acetylamino-2-trifluoromethylphenyl, 4-(1-ethoxycarbonyl)-2-nitrophenyl, 5-chloro-4-(1-ethoxycarbonylethoxy)-2-nitrophenyl,2-pyridyl, 3-pyridyl, 4-pyridyl, 3-bromo-2-pyridyl, 5-bromo-2-pyridyl, 6-bromo-2-pyridyl, 3-chloro-2-pyridyl, 5-chloro-2-pyridyl, 6-chloro-2-pyridyl, 3-fluoro-2-pyridyl, 5-fluoro-2-pyridyl, 6-fluoro-2-pyridyl, 3-cyano-2-pyridyl, 5-cyano-2-pyridyl, 6-cyano-2-pyridyl, 3-nitro-2-pyridyl, 5-nitro-2-pyridyl, 6-nitro-2-pyridyl, 3-trifluoromethyl-2-pyridyl, 4-trifluoromethyl-2-pyridyl, 5-trifluoromethyl-2-pyridyl, 6-trifluoromethyl-2-pyridyl, 3-dimethylaminocarbonyl-2-pyridyl, 3-methylsulfonyl-2-pyridyl, 3-isopropylsulfonyl-2-pyridyl, 6-chloro-3-trifluoromethyl-2-pyridyl, 3,5,6-trifluoropyridyl, 2-pyrimidinyl, 4-pyrimidinyl, 5-bromo-2-pyrimidinyl, 4-chloro-2-pyrimidinyl, 4-trifluoromethyl-2-pyrimidinyl, 4,6-dimethoxy-2-pyrimidinyl, 2,6-dimethoxy-4-pyrimidinyl or 2-quinolyl, $R_1$ and $R_2$ are as defined above.

The compounds of the formula (II-a) or their salts also can be produced by a process mentioned below.

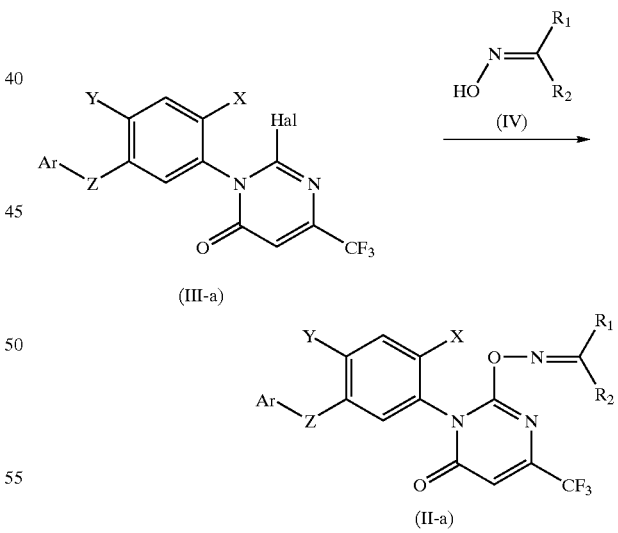

(III-a)

(II-a)

The reaction is conducted usually in the presence of a solvent and a base.

The solvent may include aromatic hydrocarbons such as benzene, toluene or xylene; aliphatic hydrocarbons such as cyclohexane or octane; ethers such as tetrahydrofuran or 1,4-dioxane; nitrites such as acetonitrile; esters such as ethyl acetate, methyl acetate; polar solvents such as N,N-dimethylformamide or dimethylsulfoxide; etc. They may be used alone as a single compound or in combination. The amount of a solvent is usually from 1 to 10 parts by volume, preferably from 3 to 5 parts by volume, per one part by weight of the compounds of the formula (II-a).

The base may be inorganic base or organic base. Examples of the inorganic bases may include alkali metal carbonates such as sodium carbonate or potassium carbonate; alkali metal bicarbonates such as sodium bicarbonate or potassium bicarbonate; alkali metal hydroxides such as sodium hydroxide or potassium hydroxide; or alkali metal hydrides such as sodium hydride. Examples of the organic bases may include trialkylamines such as trimethylamine, triethylamine; pyridine or 4-(N,N-dimethylamino)pyridine. The amount of base is usually from 0.5 to 3.0 moles, preferably from 0.5 to 1.1 moles, per one mole of the compounds of the formula (III-a).

The amount of oxime derivatives of the formula (IV) or their salts is usually from 0.9 to 3.0 moles, preferably from 1.0 to 1.1 moles, per one mole of the compounds of the formula (III-a).

The reaction temperature is usually from −10 to +200° C., preferably from 0 to +100° C.

The reaction time is usually from 30 minutes to 24 hours, preferably from 1 hour to 5 hours.

The reaction can be carried out under drying atmosphere, preferably an inert atmosphere such as nitrogen gas or argon gas.

After completion of the reaction, the product is isolated by ordinary post-treatment e.g. addition of water and extraction with an organic solvent. If necessary, the product may be purified by refinery methods such as crystallization or chromatography.

Further, the compounds of the formula (III-a) or their salts can be produced by a process mentioned below.

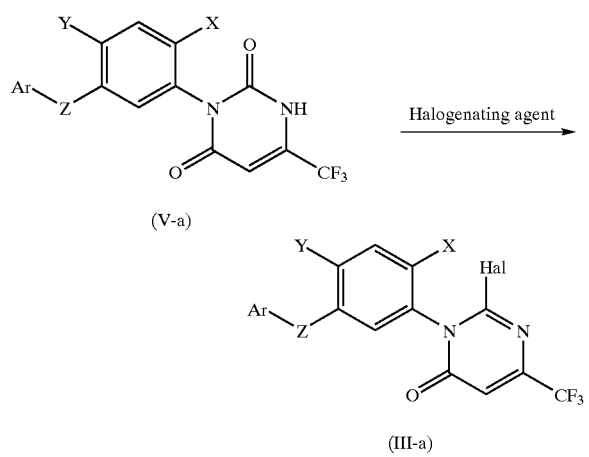

The reaction is usually conducted in the presence or absence of a solvent and in the presence of a base.

Examples of the solvent may be aromatic hydrocarbons such as benzene, toluene, xylene, mesitylene or chlorobenzene; aliphatic hydrocarbons such as cyclohexane or octane; ethers such as tetrahydrofuran or 1,4-dioxane; nitriles such as acetonitrile; esters such as ethyl acetate, methyl acetate; polar solvents such as N,N-dimethylformamide or dimethylsulfoxide; etc. They may be used alone as a single compound or in combination. The amount of a solvent is usually from 0 to 10 parts by volume, preferably from 0 to 5 parts by volume, per one part by weight of the compounds of the formula (V-a).

Examples of the base may be trialkylamines such as trimethylamine, N,N-diisopropylethylamine, triethylamine or tri-n-propylamine; pyridine or 4-(N,N-dimethylamino) pyridine. The amount of the base is usually from 0.5 to 10 moles, preferably from 1.0 to 3.0 moles, per one mole of the compounds of the formula (V-a).

Examples of the halogenating agent may be chlorinating agents such as sulfur monochloride, sulfur dichloride, thionyl chloride, sulfuryl chloride, phosphorus oxychloride, phosphorus trichloride, phosphorus pentachloride, brominating reagents such as phosphorus oxybromide, phosphorus tribromide, and the like. The amount of the halogenating agent is usually from 0.2 to 10 moles, preferably from 1.0 to 3.0 moles, per one mole of the compound of the formula (V-a).

The reaction temperature is usually from 0 to 200° C., preferably from 50 to 120° C. The reaction time is usually from 30 minutes to 24 hours.

The reaction can be carried out under drying atmosphere, preferably an inert atmosphere such as nitrogen gas or argon gas.

After completion of the reaction, the product is isolated by ordinary post-treatment e.g. addition of water and extraction with an organic solvent. If necessary, the product is purified by refining methods such as crystallization or chromatography.

The examples relating to the present invention will now be illustrated as follows.

EXAMPLES

Example 1

Preparation of 2-chloro-3-[4-chloro-2-fluoro-5-(2-nitrophenoxy)phenyl]-6-trifluoromethyl-4(3H)-pyrimidinone (Compound III-1)

A mixture of 3-[4-chloro-2-fluoro-5-(2-nitrophenoxy) phenyl]-6-trifluoromethyl-2,4(1H, 3H)-pyrimidinedione(4.5 g, 0.01 mol), phosphorus oxychloride(1.5 g, 0.01 mol), triethylamine(2.0 g, 0.02 mol) and toluene(14 ml) was heated under reflux for 24 hours. The reaction mixture was poured into water and extracted with ethyl acetate. The ethyl acetate solution contained 3.5 g(yield 76%) of the above compound III-1(HPLC analysis). The ethyl acetate solution was concentrated and purified by column chromatography on silica gel(20% ethyl acetate/hexane) to give compound III-1 as a white solid, m.p.128–131° C.

$^1$H-NMR(CDCl$_3$): δ6.84(s, 1H), 6.93(d, J=7.2 Hz, 1H), 7.00(d, J=7.2 Hz, 1H), 7.30(t, J=7.6 Hz, 1H), 7.50(d, J=8.8 Hz, 1H), 7.57(dt, J=8.4, 1.2 Hz, 1H), 8.00(dd, J=8.4, 1.2 Hz, 1H).

Example 2

Preparation of 2-chloro-3-[4-chloro-2-fluoro-5-(2-pyrimidinyloxy)phenyl]-6-trifluoromethyl-4(3H)-pyrimidinone (Compound III-2)

A mixture of 3-[4-chloro-2-fluoro-5-(2-pyrimidinyloxy) phenyl]-6-trifluoromethyl-2,4(1H,3H)-pyrimidinedione (2.01 g, 0.005 mol), phosphorus oxychloride (3.83 g, 0.025 mol), triethylamine (2.02 g, 0.02 mol and toluene (7 ml) was heated under reflux for 2 hours. The reaction mixture was poured into brine, and extracted with ethyl acetate. The organic phase was separated, dried over anhydrous sodium sulfate, and concentrated. The residue was purified by column chromatography on silica gel(40% ethyl acetate/hexane) to give compound III-2 (1.05 g, yield 49.9%) as a white solid, m.p.132–134.5° C.

$^1$H-NMR (CDCl$_3$): δ6.88(s, 1H), 7.10(t, J=4.6 Hz, 1H), 7.26(d, J=6.8 Hz, 1H), 7.47(d, J=8.8 Hz, 1H), 8.55(d, J=4.8 Hz, 2H).

Table 1 lists these compounds produced in the Examples 1 and 2, and some compounds of the formula (III-a) which are obtainable by similar processes therein.

TABLE 1

(III-a)

[Structure diagram of formula III-a with substituents Y, X, Hal, Ar, Z, and CF$_3$ pyrimidinone ring]

| Compd. | X | Y | Z | Hal | Ar |
|---|---|---|---|---|---|
| III-1 | F | Cl | O | Cl | 2-nitrophenyl |
| III-2 | F | Cl | O | Cl | 2-pyrimidinyl |
| III-3 | F | Cl | O | Cl | phenyl |
| III-4 | F | Cl | O | Cl | 3-nitro-2-pyridyl |
| III-5 | F | Cl | O | Cl | 6-fluoro-2-pyridyl |
| III-6 | H | CN | O | Cl | 2-pyrimidinyl |
| III-7 | F | Cl | S | Cl | 2-pyridyl |
| III-8 | F | Cl | S | Cl | 3-cyanophenyl |
| III-9 | F | Cl | NCH$_3$ | Cl | 2-pyrimidinyl |
| III-10 | F | Cl | O | Cl | 2-quinolyl |
| III-11 | F | NO$_2$ | O | Cl | 2-pyrimidinyl |
| III-12 | F | CF$_3$ | O | Br | 2-pyrimidinyl |

The compounds of the formula (III-a) have herbicidal activity themselves, though they are useful as an intermediate for agricultural chemicals.

Example 3

Preparation of 3-[4-chloro-2-fluoro-5-(2-nitrophenoxy)phenyl]-2-[(1-ethoxyethylidene)aminooxy]-6-trifluoromethyl-4(3H)-pyrimidinone (Compound II-1)

Ethyl N-hydroxyacetimidate(0.23 g, 0.002 mol) was added dropwise to a suspension of sodium hydride(008 g, 0.002 mol) in tetrahydrofuran(5 ml) with stirring at 0° C. 2-Chloro-3-[4-chloro-2-fluoro-5-(2-nitrophenoxy)phenyl]-6-trifluoromethyl-4(3H)-pyrimidinone(0.93 g, 0.002 mol) was added to the mixture at 0° C., and the mixture was stirred at 0° C. for 3 hours. The reaction mixture was poured into water and extracted with ethyl acetate. The ethyl acetate solution was concentrated and purified by column chromatography on silica gel(20% ethyl acetate/hexane) to give compound II-1 (0.90 g, yield 85%) as a white solid, m.p.152–155° C.

Example 4

Preparation of 3-[4-chloro-2fluoro-5-(2-nitrophenoxy)phenyl]-2-[(1-methylethylidene)aminooxy]-6-trifluoromethyl-4(3H)-pyrimidinone (Compound II-2)

A mixture of 2-chloro-3-[4-chloro-2-fluoro-5-(2-nitrophenoxy)phenyl]-6-trofluoromethyl-4(3H)-pyrimidinone(9.3 g, 0.02 mol), acetone oxime(1.5 g, 0.02 mol), potassium carbonate(2.8 g, 0.02 mol) and tetrahydrofuran(47 ml) was heated under reflux for 5 hours. The reaction mixture was poured into water and extracted with ethyl acetate. The ethyl acetate solution was concentrated and the precipitated solid was collected by filtration to give compound II-2 (7.9 g, 79%) as a white solid, m.p.156–159° C. Furthermore, the filtrate was purified by column chromatography on silica gel(33% ethyl acetate/hexane) to give compound II-2 (1.7 g, yield 17%).

Example 5

Preparation of 3-[4-chloro-2-fluoro-5-(2-nitrophenoxy)phenyl]-2-[(1-cyclopentylidene)aminooxy]-6-trifluoromethyl-4(3H)-pyrimidinone (Compound II-3)

A mixture of 2-chloro-3-[4-chloro-2-fluoro-5-(2-nitrophenoxy)phenyl]-6-trifluoromethyl-4(3H)-pyrimidinone(1.28 g, 0.0027 mol), cyclopentanone oxime (027 g, 0.0027 mol), potassium carbonate(0.38 g, 0.027 mol) and tetrahydrofuran(11 ml) was heated under reflux for 3 hours. The reaction mixture was poured into water, extracted with ethyl acetate, and washed with brine. The organic phase was dried over anhydrous sodium sulfate, and concentrated. The residue was purified by column chromatography on silica gel(20% ethyl acetate/hexane) to give compound II-3 (1.23 g, yield 84.7%) as a white amorphous solid, m.p.76–78° C.

Example 6

Preparation of 3-[4-chloro-2-fluoro-5-(2-pyrimidinyloxy)phenyl]-2-[(1-methylethylidene)aminooxy]-6-trifluoromethyl-4(3H)-pyrimidinone (Compound II-11)

A mixture of 2-chloro-3-[4-chloro-2-fluoro-5-(2-pyrimidinyloxy)phenyl]-6-trifluoromethyl-4(3H)-pyrimidinone(1.52 g, 0.0036 mol), acetone oxime(0.26 g, 0.0036 mol), potassium carbonate(0.50 g, 0.0036 mol) and tetrahydrofuran(15 ml) was heated under reflux for 5 hours. The reaction mixture was poured into brine, and extracted with ethyl acetate. The organic phase was dried over anhydrous sodium sulfate, and concentrated. The residue was purified by column chromatography on silica gel(50% ethyl acetate/hexane) to give compound II-11 (1.54 g, yield 93.3%) as a white amorphous solid, m.p 70–80° C.

Table 2 lists some representative compounds of the formula (II-a) which were prepared by Examples 3 to 6, and can be obtained by the similar processes.

TABLE 2

(II-a)

[Structure: Ar-Z-benzene(X,Y)-pyrimidinone ring with CF₃, connected to O-N=C(R₁)(R₂)]

| Compd. | R₁ | R₂ | X | Y | Z | Ar |
|---|---|---|---|---|---|---|
| II-1 | CH₃ | OCH₂CH₃ | F | Cl | O | 2-nitrophenyl |
| II-2 | CH₃ | CH₃ | F | Cl | O | 2-nitrophenyl |
| II-3 | =cyclopentylidene | | F | Cl | O | 2-nitrophenyl |
| II-4 | =cyclohexylidene | | F | Cl | O | 2-nitrophenyl |
| II-5 | CH₃ | CH₂CH₃ | F | Cl | O | 2-nitrophenyl |
| II-6[a] | CH₃ | CH₂CH₃ | F | Cl | O | 2-nitrophenyl |
| II-7 | phenyl | phenyl | F | Cl | O | 2-nitrophenyl |
| II-8 | CH₃ | phenyl | F | Cl | O | 2-nitrophenyl |
| II-9 | CH₃ | n-C₅H₁₁ | F | Cl | O | 2-nitrophenyl |
| II-10[b] | CH₃ | n-C₅H₁₁ | F | Cl | O | 2-nitrophenyl |
| II-11 | CH₃ | CH₃ | F | Cl | O | 2-pyrimidinyl |
| II-12 | =2,2-dimethyl-1,3-dioxane-4,6-dione-5-ylidene | | F | Cl | O | 2-nitrophenyl |
| II-13 | CH₃ | H | F | Cl | O | 2-nitrophenyl |
| II-14 | CH₃ | CN | F | Cl | O | 2-nitrophenyl |
| II-15 | CH₃ | COCH₃ | F | Cl | O | 2-nitrophenyl |
| II-16 | CH₃ | CF₃ | F | Cl | O | 2-nitrophenyl |
| II-17 | =cyclopentenylidene | | F | Cl | O | 2-nitrophenyl |
| II-18 | CH₃ | —CH₂CH=CH₂ | F | Cl | O | 2-nitrophenyl |
| II-19 | CH₃ | —CH₂C≡CH | F | Cl | O | 2-nitrophenyl |
| II-20 | CH₃ | CH₃ | F | Cl | O | phenyl |
| II-21 | CH₃ | CH₃ | F | Cl | O | 3-chloro-2-pyridyl |
| II-22 | CH₃ | CH₃ | F | Cl | O | 6-fluoro-2-pyridyl |
| II-23 | CH₃ | CH₃ | H | CN | O | 2-pyrimidinyl |
| II-24 | CH₃ | CH₃ | F | Cl | S | 2-pyridyl |
| II-25 | CH₃ | CH₃ | F | Cl | S | 3-cyanophenyl |
| II-26 | CH₃ | CH₃ | F | Cl | NCH₃ | 2-pyrimidinyl |
| II-27 | CH₃ | CH₃ | F | Cl | NCH₃ | 2-quinolyl |
| II-28 | CH₃ | CH₃ | F | NO₂ | O | 2-pyrimidinyl |
| II-29 | CH₃ | CH₃ | F | CF₃ | O | 2-pyrimidinyl |

[a] isomer of II-5
[b] isomer of II-9

Table 3 lists NMR data of some compounds listed in Table 2.

TABLE 3

| Compd. No. | $^1$H—NMR (CDCl$_3$)δ |
|---|---|
| II-1 | 1.33(t, J=7.2Hz, 3H), 1.79(s, 3H), 4.14–4.24(m, 2H), 6.58(s, 1H), 6.91(d, J=6.4Hz, 1H), 7.03(d, J=7.6Hz, 1H), 7.29(dt, J=8.8, 1.2Hz, 1H), 7.46(d, J=8.8Hz, 1H), 7.56(dt, J=8.4, 1.2Hz, 1H), 7.99(dd, J=8.0, 1.6Hz, 1H) |
| II-2 | 1.73(s, 3H), 2.05(s, 3H), 6.60(s, 1H), 6.88(d, J=6.4Hz, 1H), 7.04(d, J=8.0Hz, 1H), 7.30(dt, J=9.0, 1.2Hz, 1H), 7.45(d, J=8.4Hz, 1H), 7.57(dt, J=8.4, 1.6Hz, 1H), 7.99(dd, J=7.6, 1.6Hz, 1H) |
| II-3 | 1.66–1.78(m, 4H), 2.14(t, J=6.8Hz, 2H), 2.52(dd, J=7.4, 5.8Hz, 2H), 6.54(s, 1H), 7.00(d, J=8.4Hz, 1H), 7.25(dt, J=7.8, 0.8Hz, 1H), 7.41(d, J=8.8Hz, 1H), 7.50–7.55(m, 1H), 7.94(dd, J=8.4, 1.6Hz, 1H) |
| II-5 | 1.07(t, J=7.2Hz, 3H), 1.66(s, 3H), 2.31(q, J=7.5Hz, 2H), 6.50(s, 1H), 6.87(d, J=6.4Hz, 1H), 6.98(d, J=7.2Hz, 1H), 7.24(dt, J=8.0, 1.7HZ, 1H), 7.42(d, J=8.8Hz, 1H), 7.52(t, J=7.2Hz, 1H), 7.92(dd, J=8.4, 1.6Hz, 1H) |
| II-6 | 1.23(t, J=7.0Hz, 3H), 2.04(s, 3H), 2.07(t, J=6.8Hz, 2H), 6.59(s, 1H), 7.02(d, J=8.4Hz, 1H), 7.29(t, J=7.8Hz, 1H), 7.41(d, J=8.8Hz, 1H), 7.56(t, J=7.2Hz, 1H), 7.98(dd, J=8.4, 1.6Hz, 1H) |
| II-7 | 6.62(s, 1H), 6.72(d, J=6.4Hz, 1H), 6.80(d, J=8.4Hz, 1H), 7.01(d, J=8.4Hz, 2H), 7.12((d, J=8.8Hz, 1H), 7.30–7.57(m, 10H), 7.97(dd, J=8.4, 1.6Hz, 1H) |
| II-8 | 2.11(s, 3H), 6.64(s, 1H), 6.94(d, J=6.4Hz, 1H), 7.06(dd, J=8.4, 1.2Hz, 1H), 7.29(t, J=7.8Hz, 1H), 7.39–7.50(m, 4H), 7.58(t, J=7.0Hz, 1H), 7.69(dd, J=9.4, 2.2Hz, 2H), 7.98(dd, J=8.4, 1.6Hz, 1H) |
| II-9 | 0.87(brt, J=6.6Hz, 3H), 1.28–1.32(m, 4H), 1.51–1.54(m, 2H), 1.70(s, 3H), 2.32(t, J=7.6Hz, 2H), 6.59(s, 1H), 6.89(d, J=6.4Hz, 1H), 7.03(d, J=8.4Hz, 1H), 7.29(t, J=7.8Hz, 1H), 7.45(d, J=8.0Hz, 1H), 7.57(t, J=8.2Hz, 1H), 7.98(dd, J=8.2, 1.8Hz, 1H) |
| II-10 | 0.81(t, J=7.4Hz, 3H), 0.97–1.27(m, 6H), 1.97(s, 3H), 1.97–2.08(m, 2H), 6.55(s, 1H), 6.88(d, J=6.4Hz, 1H), 6.97(d, J=8.8Hz, 1H), 7.24(t, J=8.8Hz, 1H), 7.41(d, J=8.8Hz, 1H), 7.52(dt, J=8.1, 1.3Hz, 1H), 7.93(dd, J=8.4, 1.6Hz, 1H) |
| II-11 | 1.75(s, 3H), 2.04(s, 3H), 7.08(t, J=5.0Hz, 1H), 7.25(d, J=5.2Hz, 1H), 7.42(d, J=8.8Hz, 1H), 8.52(d, J=4.8Hz, 1H) |

The compounds of the formula (II-a) have herbicidal activity themselves, though they are useful as an intermediate for agricultural chemicals.

Example 7

Preparation of 3-[4-chloro-2-fluoro-5-(2-nitrophenoxy)phenyl]-1-[(1-methylethylidene)amino]-6-trifluoromethyl-2,4(1H, 3H)-pyrimidinedione (Compound I-1)

3-[4-Chloro-2-fluoro-5-(2-nitrophenoxy)phenyl]-2-[(1-methylethylidene)aminooxy]-6-trifluoromethyl-4(3H)-pyrimidinone(0.5 g, 0.001 mol) was heated at 170° C. for 1 hour. This reactant contained 0.22 g(yield 45%) of the above compound (HPLC analysis). This reactant was purified by column chromatography on silica gel(33%ethyl acetate/hexane) to give compound I-1 as a white solid, m.p.173–176° C.

$^1$H-NMR(CDCl$_3$): δ1.97(s, 3H), 2.26(s, 3H), 6.34(s, 1H), 6.93(d, J=8.4 Hz, 1H), 7.07(d, J=6.5 Hz, 1H), 7.23(dt, J=7.4, 1.0 Hz, 1H), 7.42(d, J=8.8 Hz, 1H), 7.52(dt, J=8.2, 1.7 Hz, 1H), 7.98(dd, J=8.1 Hz, 1.6 Hz, 1H).

Example 8

Preparation of 3-[4-chloro-2-fluoro-5-(2-nitrophenoxy)phenyl]-1-[(1-ethoxyethylidene)amino]-6-trifluoromethyl-2,4(1H, 3H)-pyrimidinedione (Compound I-2)

3-[4-Chloro-2-fluoro-5-(2-nitrophenoxy)phenyl]-2-[(1-ethoxyethylidene)aminooxy]-6-trifluoromethyl-4(3H)-pyrimidinone(0.27 g, 0.5 mmol) was heated at 170° C. for 2 hours. This reactant was purified by column chromatography on silica gel(20% ethyl acetate/hexane) to give compound 1–2 (0.14 g, yield46%) as a yellow amorphous solid, m.p.52–56° C.

$^1$H-NMR(CDCl$_3$): δ1.34(t, J=7.6 Hz, 3H), 1.95(s, 3H), 4.28–4.33(m, 2H), 6.30(s, 1H), 6.90(d, J=8.4 Hz, 1H), 7.06(d, J=6.4 Hz, 1H), 7.21(dt, J=8.4, 0.8 Hz, 1H), 7.41(d, J=8.8 Hz, 1H), 7.50(dt, J=7.6, 1.2 Hz, 1H), 7.96 (dd, J=8.4, 2.0 Hz, 1H).

Example 9

Preparation of 3-[4-chloro-2-fluoro-6-(2-nitrophenoxy)phenyl]-1-[(1-cyclopentylideneamino]-6-trifluoromethyl-2,4(1H, 3H)-pyrimidinedione (Compound I-3)

A mixture of 3-[4-chloro-2-fluoro-5-(2-nitrophenoxy)phenyl]-2-[(1-cyclopentylidene-aminooxy-6-trifluoromethyl-4(3H)-pyrimidinone(0.216 g, 0.41 mmol) and toluene(2 ml) was heated under reflux for 2.5 hours. The mixture was concentrated, and purified by column chromatography on silica gel(30% ethyl acetate/hexane) to give compound I-3 (0.097 g, 44.9%) as a white solid.

$^1$H-NMR(CDCl$_3$): δ1.89–1.96(m,4H), 2.41(t, J=7.0 Hz, 2H), 2.68–2.72(m, 2H), 6.33(s, 1H), 6.94(dd, J=8.4, 0.8 Hz, 1H), 7.10(d, J=6.4 Hz, 1H), 7.24(t, J=8.4 Hz, H), 7.44(d, J=8.8 Hz, 1H), 7.53(t, J=7.0 Hz, 1H), 7.99(dd, J=8.0, 1.6 Hz, 1H).

Example 10

The Following Compounds I-4 to I-10 were Synthesized in a Similar Manner as Example 8, by Using Different Compounds of the Formula (II-a) as Starting Material Compound I-4: 3-[4-chloro-2-fluoro-5-(2-nitrophenoxy)phenyl]-1-[(1-cyclohexyldene-amino]-6-trifluoromethyl-2,4(1H, 3H)-pyrimidinedione.

Yield: 44.9%.

$^1$H-NMR(CDCl$_3$): δ1.41–2.56(m, 10H), 6.33(s, 1H), 6.93 (d, J=8.4 Hz, 1H), 7.09(d, J=6.0 Hz, 1H), 7.22(t, J=7.8 Hz, 1H), 7.42(d, J=8.8 Hz, 1H), 7.51(t, J=7.0 Hz, 1H), 7.96(d, J=8.0 Hz, 1H).

Compound I-5: 3-[4-chloro-2-fluoro-5-(2-nitrophenoxy)phenyl]-1-[(1-methylpropyl-idene)amino]-6-trifluoromethyl-2,4(1H, 3H)-pyrimidinedione.

Compound I-6: 3-[4-chloro-2-fluoro-5-(2-nitrophenoxy)phenyl]-1-[(1-methylpropylidene)-amino]-6-trifluoromethyl-2,4(1H, 3H)-pyrimidinedione (isomer of compound I-5).

Yield: 38.9% (total of I-5 and I-6).

$^1$H-NMR(CDCl$_3$): δ1.19(t, J=7.2 Hz, 3H), 1.93(s, 3H), 2.52(q, J=6.9 Hz, 2H), 6.90(d, J=8.4 Hz, 1H), 7.05(d, J=6.4 Hz, 1H), 7.20(t, J=7.4 Hz, 1H), 7.40(d, J=8.8 Hz, 1H), 7.49(t, J=7.0 Hz, 1H), 7.95(dd, J=8.4, 1.6 Hz, 1H)

Compound I-7: 3-[4-chloro-2-fluoro-5-(2-nitrophenoxy)phenyl]-1-[(1-methylhexylidene)-amino]-6-trifluoromethyl-2,4(1H, 3H)-pyrimidinedione.

Compound I-8: 3-[4-chloro-2-fluoro-5-(2-nitrophenoxy)phenyl]-1-[(1-methylhexylidene)-amino]-6-trifluoromethyl-2,4(1H, 3H)-pyrimidinedione (isomer of compound I-7).

Yield: 33.8% (total of I-7 and I-8).

$^1$H-NMR(CDCl$_3$): δ0.82(t, J=6.8 Hz, 3H), 1.26–1.32(m, 4H), 1.54–1.61(m, 2H), 1.87(s, 3H), 2.43(t, J=7.8 Hz, 2H), 6.25(s, 1H), 6.85(d, J=8.8 Hz, 1H), 7.00(d, J=6.4 Hz, 1H), 7.14(t, J=7.2 Hz, 1H), 7.34(d, J=8.8 Hz, 1H), 7.43(t, J=7.2 Hz, 1H), 7.88(dd, J=8.4, 1.6 Hz, 1H).

Compound I-9: 3-[4-chloro-2-fluoro-5-(2-pyrimidinyloxy)phenyl]-1-[(1-methylethylidene)amino]-6-trifluoromethyl-2,4(1H, 3H)-pyrimidinedione.

Yield: 19.9% (HPLC-area %).

$^1$H-NMR(CDCl$_3$): δ1.96(s, 3H), 2.24(s, 3H), 6.34(s, 1H), 7.05(t, J=5.0 Hz, 1H), 7.28(s, 1H), 7.38(d, J=8.8 Hz, 1H), 8.54(d, J=4.8 Hz, 2H).

Compound I-10: 3-[4-chloro-2-fluoro-5-(2-pyrimidinyloxy)phenyl]-1-[(1-cyclopentylidene-amino]-6-trifluoromethyl-2,4(1H, 3H)-pyrimidinedione.

$^1$H-NMR(CDCl$_3$): δ1.77–1.90(m, 4H), 2.36–2.39(m, 2H), 2.64–2.67(m, 2H), 6.31(s, 1H), 7.04(t, J=4.6 Hz, 1H), 7.23(d, J=3.6 Hz, 1H), 7.37(d, J=8.8 Hz, 1H), 8.53(d, J=4.8 Hz, 2H).

The compounds of formula (I), particularly of formula (I-a) are useful as a precursor of certain ingredient of herbicides.

Namely, the compounds of the general formula (I-a) can be optionally used in the reactions for changing the group; —N═C(R$_1$)(R$_2$) in the chemical structure of the general formula (I-a) to the amino group; —NH$_2$. For example, the reaction is carried out by reacting compounds of general formula (I-a) with an aqueous solution of mineral acid such as hydrochloric acid in the presence of alcohol such as methanol at a temperature of from 0° C. to 150° C., usually under reflux conditions. The compounds obtained are useful as herbicides, defoliants or desiccants, particularly herbicides for controlling undesired weeds in cropland.

The preparation example using such reaction will be illustrated as follows.

A suspension of 3-[4-chloro-2-fluoro-5-(2-nitrophenoxy)phenyl]-1-[(1-methylethylidene)-amino]-6-trifluoromethyl-2,4(1H, 3H)-pyrimidinedione (0.300 g, 0.60 mmol), 1 N HCl (3.0 mL), and methanol (3.0 mL) was heated to reflux for 2 hours. The reaction was cooled to room temperature, partitioned between water and ethyl acetate, and the phases separated. The aqueous phase was extracted ethyl acetate (3×50 mL) and concentrated. Chromatography (20% ethyl acetate/hexane) of the residue afforded 1-amino-3-[4-chloro-2-fluoro-5-(2-nitrophenoxy)-phenyl]-6-trifluoromethyl-2,4(1H,3H)-pyrimidinedione 0.12 g (43.5%) of a white solid. $^1$H-NMR (CDCl$_3$): δ 4.58 (bs, 2H), 6.25 (s, 1H), 6.94 (dd, J=8.38, 1.13 Hz, 1H), 7.03 (d, J=6.52 Hz, 1H), 7.24 (dt, J=7.29, 1.22 Hz, 1H), 7.43 (d, J=8.83 Hz, 1H), 7.53 (dt, J=7.12, 1.69 Hz, 1H), 7.97 (dd, J=8.15, 1.65 Hz, 1H).

We claim:

1. A method for producing a compound of the formula (I) or its salt:

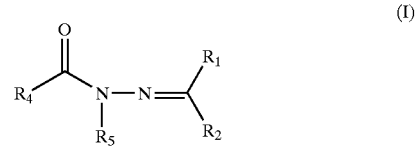

(I)

wherein each of R$_1$ and R$_2$ is hydrogen, unsubstituted or substituted alkyl, unsubstituted or substituted alkenyl, unsubstituted or substituted alkynyl, unsubstituted or substituted aryl, OR$_3$, COR$_3$, or cyano; R$_3$ is unsubstituted or substituted alkyl, unsubstituted or substituted alkenyl, unsubstituted or substituted alkynyl, unsubstituted or substituted aryl, or unsubstituted or substituted heteroaryl;

R$_1$ and R$_2$ may combine together with the adjacent carbon atom of ═CR$_1$R$_2$ to form an unsubstituted or substituted cyclic ring;

each of R$_4$ and R$_5$ is hydrogen, unsubstituted or substituted alkyl, unsubstituted or substituted alkenyl, unsubstituted or substituted alkynyl, unsubstituted or substituted aryl, unsubstituted or substituted heteroaryl, NR$_6$R$_7$, OR$_8$ or SR$_9$; each of R$_6$, R$_7$, R$_8$ and R$_9$ is hydrogen, unsubstituted or substituted alkyl, unsubstituted or substituted alkenyl, unsubstituted or substituted alkynyl, unsubstituted or substituted aryl, or unsubstituted or substituted heteroaryl, unsubstituted or substituted alkylcarbonyl, unsubstituted or substituted alkenylcarbonyl, unsubstituted or substituted alkynylcarbonyl, unsubstituted or substituted arylcarbonyl, or unsubstituted or substituted heteroarylcarbonyl;

R$_4$ and R$_5$ may combine together with the adjacent skeleton of C/N bond to form a heterocyclic ring;

which comprises rearranging a compound of the formula (II) or its salt:

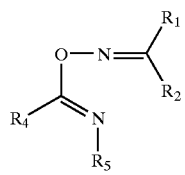

(II)

wherein R₁, R₂, R₄ and R₅ are as defined above.

2. A process for producing a 1-substituted amino-2,4(1H,3H)-pyrimidinedione of the formula (I-a) or its salt:

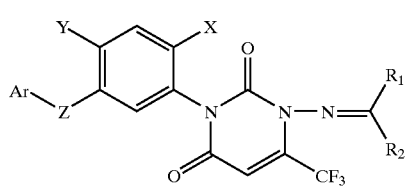

(I-a)

wherein each of R₁ and R₂ is hydrogen, unsubstituted or substituted alkyl, unsubstituted or substituted alkenyl, unsubstituted or substituted alkynyl, unsubstituted or substituted aryl, OR₃, COR₃, or cyano; R₃ is unsubstituted or substituted alkyl, unsubstituted or substituted alkenyl, unsubstituted or substituted alkynyl, unsubstituted or substituted aryl, or unsubstituted or substituted heteroaryl;

R₁ and R₂ may combine together with the adjacent carbon atom of =CR₁R₂ to form an unsubstituted or substituted cyclic ring;

each of X and Y is hydrogen, halogen, cyano, nitro, thiocarbamoyl or haloalkyl;

Z is oxygen, sulfur or NR; R is hydrogen, alkyl, alkenyl or alkynyl; and

Ar is unsubstituted or substituted aryl, or unsubstituted or substituted heteroaryl;

which comprises rearranging a 2-(substituted aminooxy)-4-(3H) pyrimidinone of the formula (II-a) or its salt:

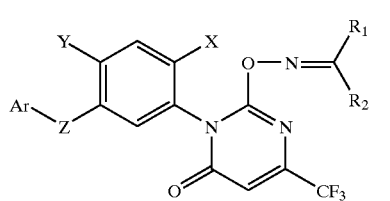

(II-a)

wherein R₁, R₂, X, Y, Z and Ar are as defined above.

3. The process according to claim 2, which comprises 1) reacting a 2-halogeno-4-(3H) pyrimidinone of the formula (III-a) or its salt:

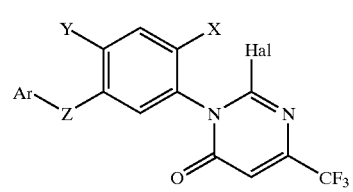

(III-a)

wherein Hal is halogen, and X, Y, Z and Ar are as defined in claim 2, with a oxime derivatiive of the formula (IV) or its salt:

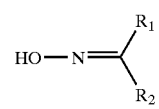

(IV)

wherein R₁ and R₂ are as defined in claim 2 to produce 2-(substituted aminooxy)-4-(3H) pyrimidinone of the formula (II-a) or its salt, and 2) rearranging the compound of the formula (II-a) or its salt.

4. The process according to claim 2, which comprises, 1) reacting a 2,4(1H,3H)-pyrimidinedione of the formula (V-a) or its salt:

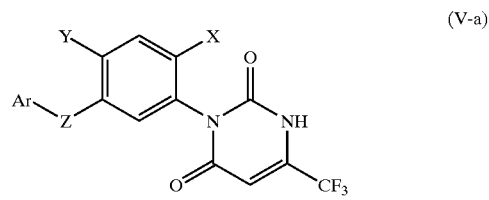

(V-a)

wherein X, Y, Z and Ar are as defined in claim 2, with a halogenating reagent to produce a 2-chloro-4-(3H) pyrimidinone of the formula (III-a) or its salt:

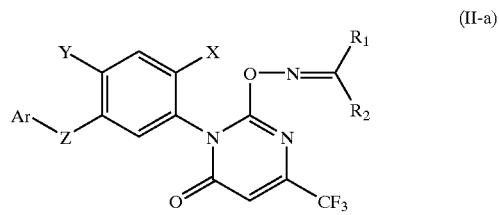

(II-a)

wherein Hal, X, Y, Z and Ar are as defined in claim 2, 2) reacting the compounds of the formula (III-a) or its salt with a oxime derivative of the formula (IV) or its salt:

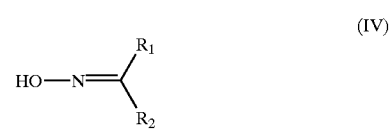

(IV)

wherein R₁ and R₂ are as defined in claim 2 to produce a 2-(substituted aminooxy)4-(3H) pyrimidinone of the formula (II-a) or its salt, and 3) rearranging the compound of the formula (II-a) or its salt.

* * * * *